United States Patent
Delgado Alonso et al.

(10) Patent No.: US 11,202,590 B2
(45) Date of Patent: Dec. 21, 2021

(54) SENSOR INTEGRATED BIOPSY NEEDLE SYSTEM

(71) Applicant: Intelligent Optical Systems, Inc., Torrance, CA (US)

(72) Inventors: Jesus Delgado Alonso, Torrance, CA (US); Robert Lieberman, Torrance, CA (US); David Berry, Torrance, CA (US)

(73) Assignee: Intelligent Optical Systems, Inc., Torrance, CA (US)

( * ) Notice: Subject to any disclaimer, the term of this patent is extended or adjusted under 35 U.S.C. 154(b) by 0 days.

(21) Appl. No.: 15/610,822

(22) Filed: Jun. 1, 2017

(65) Prior Publication Data

US 2018/0360353 A1 Dec. 20, 2018

Related U.S. Application Data

(60) Provisional application No. 62/483,436, filed on Apr. 9, 2017.

(51) Int. Cl.
| | | |
|---|---|---|
| *A61B 5/1459* | (2006.01) | |
| *A61B 5/00* | (2006.01) | |
| *A61B 5/145* | (2006.01) | |
| *A61B 10/02* | (2006.01) | |

(52) U.S. Cl.
CPC ........ *A61B 5/1459* (2013.01); *A61B 5/14532* (2013.01); *A61B 5/6848* (2013.01); *A61B 10/0233* (2013.01)

(58) Field of Classification Search
None
See application file for complete search history.

(56) References Cited

U.S. PATENT DOCUMENTS

| | | | | |
|---|---|---|---|---|
| 5,384,097 A | * | 1/1995 | Brouwer | ............ A61B 10/0038 206/446 |
| 5,769,791 A | * | 6/1998 | Benaron | ............... A61B 5/0084 600/473 |
| 5,995,686 A | | 11/1999 | Hamberger et al. | |
| 6,205,263 B1 | | 3/2001 | Lieberman et al. | |
| | | (Continued) | | |

FOREIGN PATENT DOCUMENTS

WO    WO-2011152747 A1 * 12/2011 ......... G01N 21/1702

OTHER PUBLICATIONS

San Martin et al. A Genetically Encoded FRET Lactate Sensor and Its Use To Detect the Warburg Effect in Single Cancer Cells; PLoS One 8(2): e57712 (Year: 2013).*

(Continued)

*Primary Examiner* — Kaylee R Wilson
*Assistant Examiner* — Jay B Shah
(74) *Attorney, Agent, or Firm* — Brian Billett

(57) ABSTRACT

Disclosed is a system which adds biochemical sensitivity to a standard biopsy needle such that the practitioner is provided immediate feedback on the metabolism and physiology of tissue in the local environment. Disclosed is a sensor integrated biopsy device for in situ and real time tissue analysis. The sensor integrated biopsy (SIB) needle system will enable biopsy teams to measure local tissue biochemistry in real time during biopsy procedures, adding a valuable new set of parameters to augment and extend conventional image-guided procedures.

11 Claims, 16 Drawing Sheets

(56) References Cited

U.S. PATENT DOCUMENTS

| | | | | |
|---|---|---|---|---|
| 2002/0197456 | A1* | 12/2002 | Pope | G02F 1/133617 |
| | | | | 428/209 |
| 2003/0208154 | A1* | 11/2003 | Close | A61B 5/1459 |
| | | | | 604/65 |
| 2003/0231818 | A1* | 12/2003 | Cantin | G01D 5/35383 |
| | | | | 385/12 |
| 2006/0167416 | A1* | 7/2006 | Mathis | A61B 10/0275 |
| | | | | 604/164.01 |
| 2010/0317964 | A1* | 12/2010 | Hendriks | A61B 5/0075 |
| | | | | 600/424 |
| 2018/0031485 | A1 | 2/2018 | Delgado Alonso et al. | |

OTHER PUBLICATIONS

Stavroulis et al. Methods for specimen removal from the peritoneal cavity after laparoscopic excision; 2013 Royal College of Obstetricians and Gynaecologists; 15:26-30 (Year: 2013).*

Unpublished U.S. Appl. No. 14/089,627, filed Nov. 25, 2013, "Gas Sensing Chemistry and Sensors and Sensor Systems and Method." Office Action dated Jun. 26, 2018.

Unpublished U.S. Appl. No. 14/089,627, filed Nov. 25, 2013, "Gas Sensing Chemistry and Sensors and Sensor Systems and Method." Notice of Allowance dated Apr. 26, 2019.

* cited by examiner

SENSOR INTEGRATED BIOPSY NEEDLE SYSTEM

RELATED APPLICATIONS

This application for patent claims the benefit of provisional application 62/483,436, filed on Apr. 9, 2017. The application is incorporated herein in its entirety.

GOVERNMENT LICENSE RIGHTS

This invention was made with government support under contract #NIH HHSN261201600029C awarded by the National Institute of Health. The government has certain rights in the invention.

FIELD OF THE INVENTION

This field of this disclosure relates generally to medical biopsy systems.

BACKGROUND

Although current image-guided needle biopsies are generally adequate for the collection of material for conventional histopathological analysis, gathering tissue for the detailed molecular analysis needed to truly optimize cancer treatment can be difficult. This is because ultrasound and x-ray images give virtually no information on local tissue chemistry, and even advanced magnetic resonance imaging—despite fabulously expensive equipment—have only limited chemical characterization capabilities. Thus the acquisition of samples with high concentrations of viable tumor cells—extremely important for the accurate biomolecular analysis and characterization of neoplastic tissue—is a hit-or-miss process for biopsies guided in these ways. Adding biochemical sensitivity to the biopsy needle can give the practitioner immediate feedback on the metabolism and physiology of tissue in the local environment, information that can be related to tumor activity. For example, tumor oxygenation has been tentatively shown to be predictive of response to chemotherapy, low pH is associated with rapid tumor growth, and pathophysiologic lactate accumulation is characteristic of solid tumors and has been associated with metastases and poor overall survival in cancer patients. Oxygenation, pH, and lactate levels monitoring enable monitoring tissue metabolism, and in particular glycolysis. It has been observed that most if not all cancer cells, even those in normotic tumors, produce energy by glycolysis (Warburg-like effect) The glycolytic metabolism of cancer was underappreciated for almost a century until the recent recognition of the fundamental role of glycolysis in cancer growth and progression. This has led the scientific community to adopt differential tumor metabolism as an additional hallmark of cancer Early detection of cancer greatly increases the chances for successful treatment. Approximately 8 million suspicious lesions per annum are discovered by initial screening in the US. Of these, physicians select approximately 1.3 million for biopsy. Breast cancer biopsies in the U.S. average approximately $2,620 per patient, which includes appropriate weighting factors for the number of surgical and core needle procedures performed. The combination of these figures gives a clear view of the significance of continuous developing of advanced biopsy techniques, and the potential market.

BRIEF DESCRIPTION OF THE DRAWINGS

(FIG. 8A) 5 mm before inserting the needle in the tumor (control), (FIG. 8B) the edge of the tumor (tumor edge) and (FIG. 8C) inside the tumor (inside tumor).

DESCRIPTION

Figures 1A, 1B:
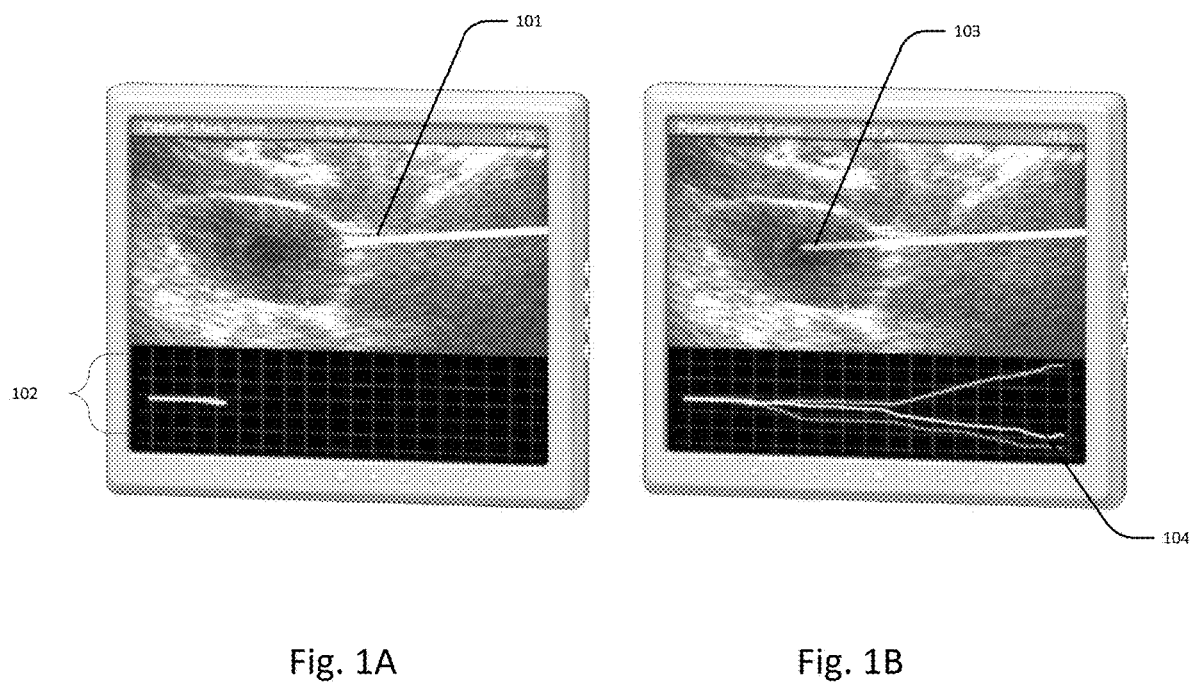
FIGS. 1A and 1B show the exemplar sensor and guiding imaging outputs for the disclosed system.

Disclosed is a system which adds biochemical sensitivity to a standard biopsy needle such that the practitioner is provided immediate feedback on the metabolism and physiology of tissue in the local environment.

Disclosed is a sensor integrated biopsy device for in situ and real time tissue analysis. The sensor integrated biopsy (SIB) needle system will enable biopsy teams to measure local tissue biochemistry in real time during biopsy procedures, adding a valuable new set of parameters to augment and extend conventional image-guided procedures.

Disclosed is a system which can monitor and quantify in real time glycolysis (Warburg-like effect) during a biopsy procedure, even in normotic tumors. It has been observed that most, if not all, cancer cells, even those in normotic tumors, produce energy by glycolysis. This feature differentiates aspects of the current disclosure from others.

Disclosed is a system which can monitor in real time the biochemistry within the tumor microenvironment (TME), which can increase the pace of TME-targeted drug discovery and may improve early stage diagnosis, prognosis assessment, prediction of effective therapy, and therapy modulation during treatment. Technologies based on the physical properties of tissue cannot provide this information.

In various embodiments, the disclosed SIB probe is virtually indistinguishable from a conventional biopsy needle set. The disclosed SIB probe contains multiple optical fiber chemical sensors that continuously transmit information on physiological chemical levels in the immediate vicinity of the tip. In practice the biopsy team can use this information to guide sample collection, optimizing the effectiveness of the procedure, minimizing the need for repeat biopsy, and assuring that tissue samples are recovered from high tumor content areas and any other regions of interest In various embodiments, as the needle progresses into the patient's body, real-time biochemical information lets the surgeon know as soon as the needle has encountered the margin of a tumor and tumor tissue, because tumor tissue has a different "biochemical signature" than healthy tissue. For example, tumor oxygenation has been tentatively shown to be predictive of response to chemotherapy, low pH which is associated with rapid tumor growth and pathophysiologic lactate accumulation is characteristic of solid tumors and has been associated with metastases and poor overall survival in cancer patients. This real-time biochemical information will help the surgeon place the needle in regions of maximum tumor cellularity within the biopsied region, and guide precise cutting and removal of tumor masses.

In various embodiments, once a high-quality sample is obtained, genetic analysis and other techniques can determine the "molecular signature" of the malignant material. This in turn enables the treating physician to tightly target treatment to the specific strain of cancer found, and to follow the course of treatment with an unprecedented level of accuracy. SIB needle biopsies will collect the samples needed to accomplish this advance in treatment.

Figure 3:
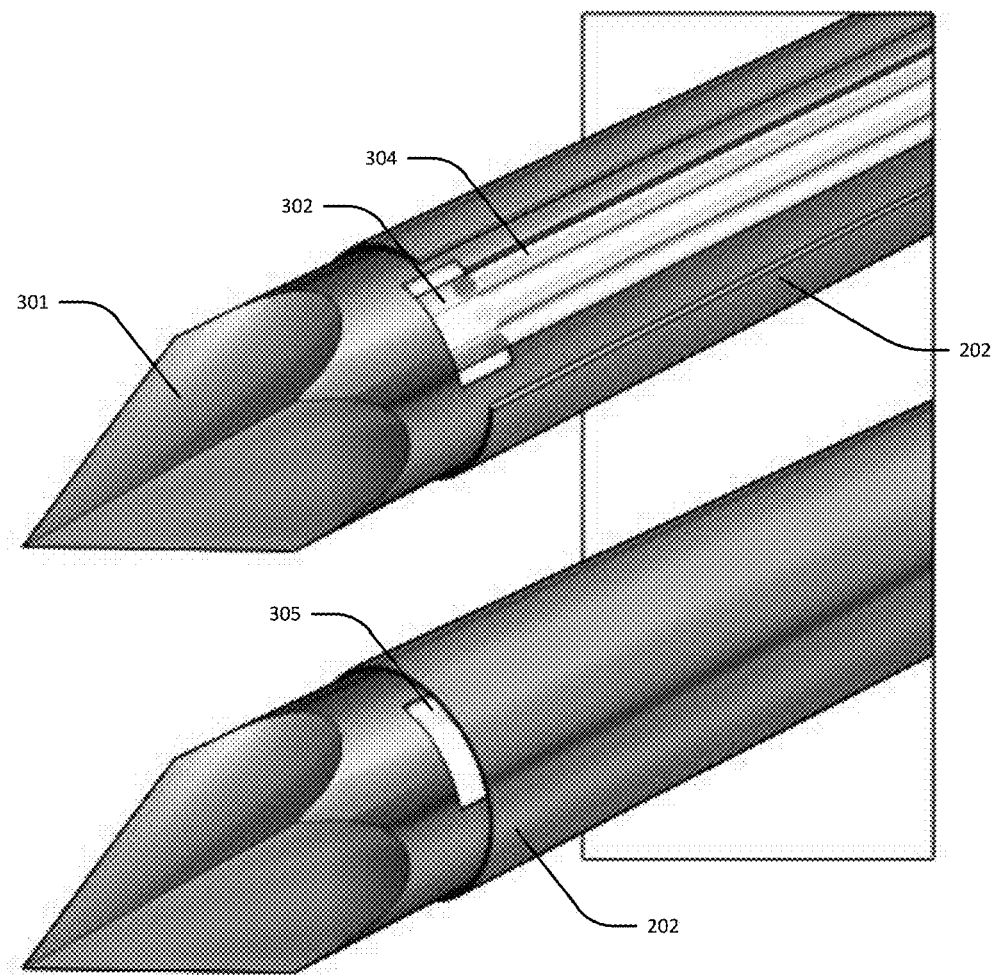
FIG. 3 shows close-up views of the disclosed sensor integrated biopsy needle.

A differentiating factor of various embodiments is the capability of the SIB needle system to deliver real-time biochemical information, asset glycolysis, during biopsy by a suite of tiny optical fiber chemical sensors integrated into the trocar of the coaxial needle through which the biopsy is carried out. In the disclosed SIB needles, the standard trocar is replaced by a trocar designed as a hollow tube capable of integrating up to six optical fibers, with a solid sharp tip to maintain its cutting capability. FIG. 3 illustrates a view of the assembled SIB needle showing three embedded optical sensor elements.

FIGS. 1A and 1B show monitors presenting real time chemical information during biopsy procedure, in addition to standard images from the ultrasound system. Shown in FIG. 1A is baseline sensor data 102 reporting the position of the needle 101 out of the tumor. Shown in FIG. 1B is sensor data 104 detecting, in real time, needle 103 approximation to tumor margin and insertion in the tumor.

Figure 2:
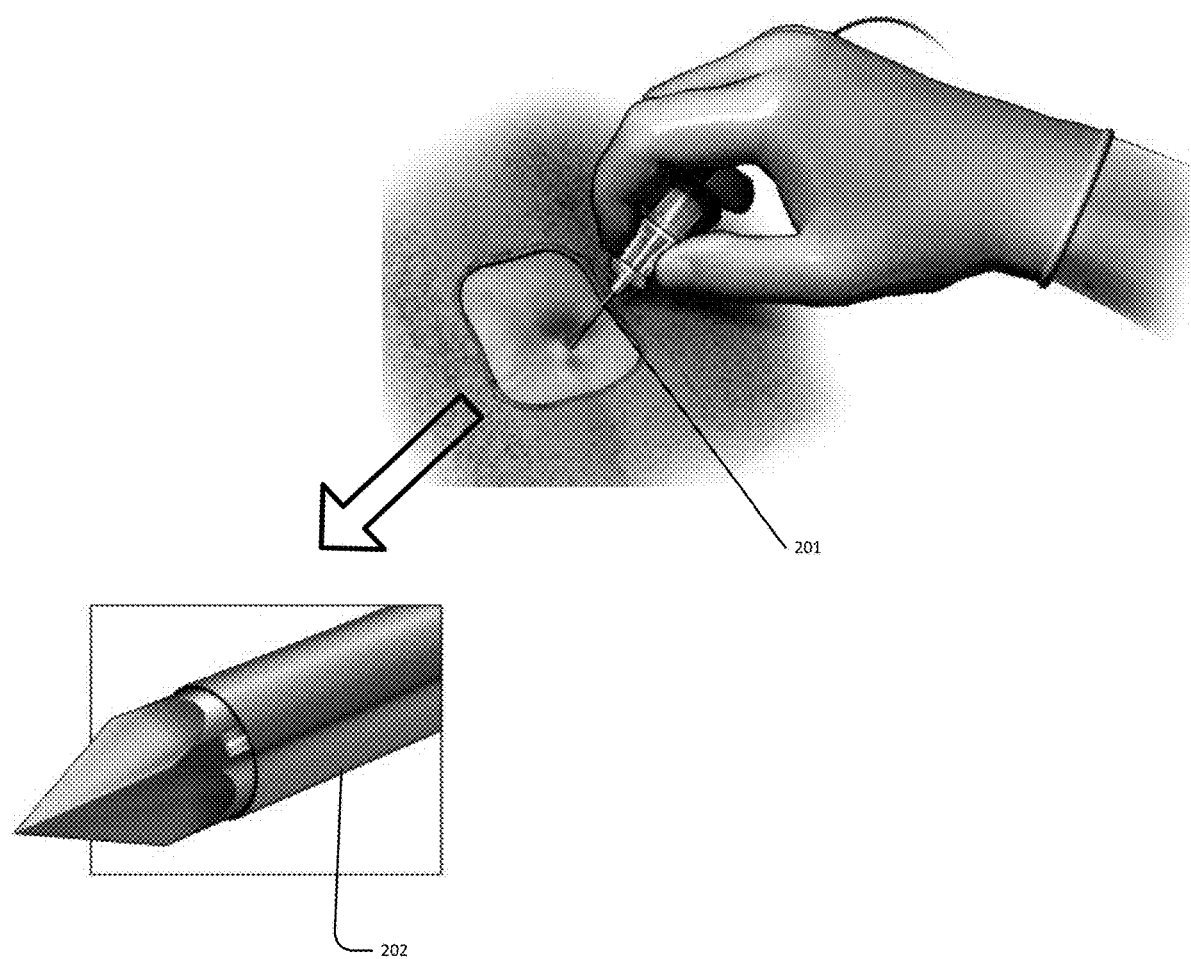
FIG. 2 shows a close-up of the disclosed sensor integrated biopsy needle and a view during typical use.

FIG. 2 shows the application of a basic embodiment depicting the fiber optic sensors 201 and the use of the sensor integrated biopsy needle 202.

FIG. 3 shows an embodiment design of the sensor integrated trocar, showing the interior of the hollow trocar where plastic optical fibers 304 are placed. The small sensor window 305 covered by a medical grade permeable material is the only external difference with a standard coaxial needle 202.

Figure 4:
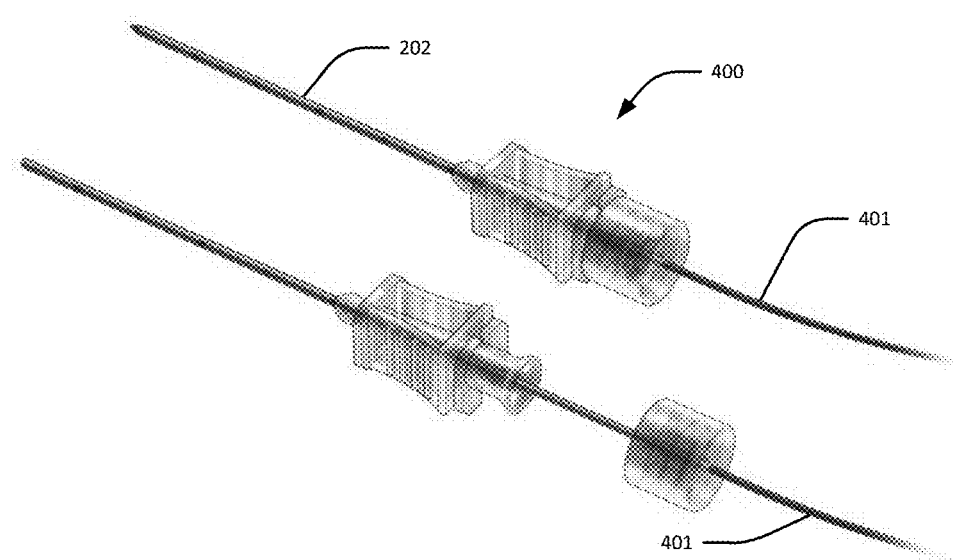
FIG. 4 shows a view of the disclosed sensor integrated biopsy needle with the trocar and optical sensor components of the disclosed system.

In various embodiments the SIB needle is assembled by introducing optical fibers inside the trocar, with the tip of each fiber functionalized for pH, oxygen, or lactate monitoring. The hollow trocar 301 has a small "window" 305 milled into its side, very close to its tip, to expose the sensor tips 302 to tissue. The fiber optic sensor tips (sensor elements) 302 are placed in that "window." To create the permeable segment for sensor exposure to the tissue, the open side will be filled with a biocompatible, medical grade permeable material that will accomplish two functions: (1) it will maintain the cylindrical shape of the trocar, but still allow the target analytes to diffuse towards the sensors; (2) it will assure the biocompatibility of the sensor segment. Only a few tenths of a millimeter of the sensor "window" is actually exposed to the tissue; most of the "window" is covered by the coaxial needle. T As shown in FIG. 4, at the other end of the trocar is a connector 400 through which the sensor integrated trocar connects with a compact readout unit via a plastic optical fiber 401. The external design of a standard coaxial biopsy needle and that of the SIB needle are almost identical. The only differences are the small area of permeable polymer close to the tip, and the optical fiber on the other end. The actual difference is only in its interior (the heart of the SIB needle), where the sensor material is contained. The SIB needle functions as a standard coaxial needle, and the readings are generated without any additional action by the person performing the biopsy.

In accordance with the standard biopsy procedure, the coaxial introducer needle with the trocar is inserted, guided by imaging, and with the SIB needle is guided by real-time monitoring of the selected biomarkers as well. Once the monitoring determines that the needle is in potential tumor tissue, the needle is secured and the trocar is removed, leaving space for insertion of the cutting cannula needle that takes the tissue sample.

Integrating the sensor with the coaxial introducer needle instead of the cutting cannula needle has significant advantages:

(1) It is simple to fabricate (hence lower in cost).
(2) It senses the tissue in the exact area from which the sample tissue will be collected, assuring the quality of the sample.
(3) Only the trocar is modified, so the SIB needle will be compatible with all current coaxial introducer needles (facilitating market entry and IRB approval), and therefore with any biopsy needle, including vacuum-assisted biopsy needles, and
(4) Medical personnel will not need additional training to handle the sensor integrated biopsy device, since its use and design are the same as for regular coaxial needles.

Figure 5:
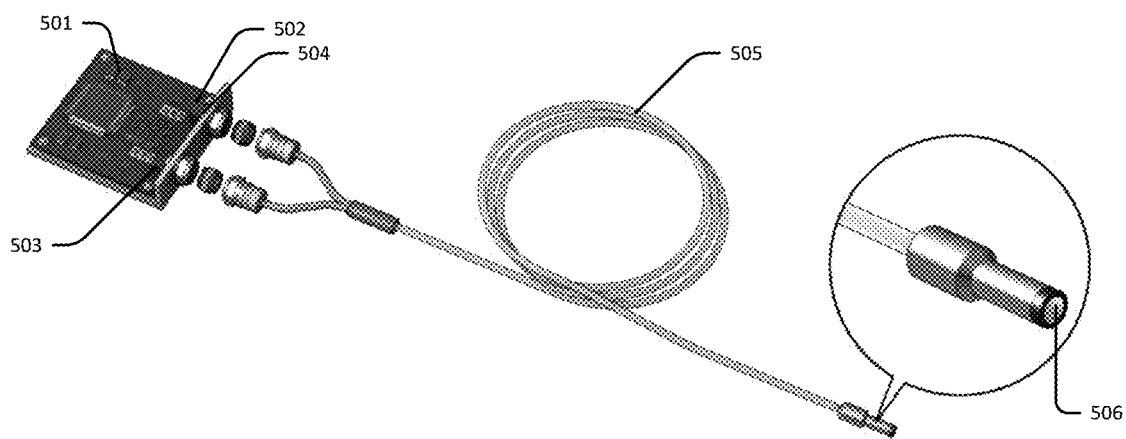
FIG. 5 shows some the of the main components of a fiber optic chemical sensor system.

The heart of a fiber optic chemical sensor 506 shown in FIG. 5 is a chemically-sensitive material in which a specific indicator molecule has been immobilized in a polymer substrate (sensor material). In response to a selective interaction between the target analyte (e.g., oxygen, pH, or lactate) and the indicator, the luminescence of the sensitive material undergoes a measurable change proportional to the analyte concentration. In the case of biosensors, like the lactate sensors, a biomolecule, for example an enzyme, is also immobilized in the sensor material. The biomolecule will react with the target analyte, and a result of that reaction the chemical composition in the sensor material will change. That chemical change is monitored by a chemical transducer, and it related to the analyte concentration. The biomolecule can be immobilized together with the chemical transducer or the biosensor can be made with multiple layers, one consists of the chemical transducer and one of the biological materials. The proposed optical sensors will be based on sensor materials placed at the tips of optical fibers, and multiple different fibers will be used in each SIB needle. FIG. 5 also shows other components of the system, including the optical fiber lead 505, the LED light source 503, the photodetector 502, optical filters 504, and the electronics module 501 for processing the light source signals and detected optical signals.

In various embodiments, the measured emission intensity from the sensor element is affected by fluctuations in the excitation source intensity, and by the detector response, dimensions of the optical fibers, manipulation of the optical fiber, and variation in the thickness of the sensor element. In contrast, time domain measurements that rely on the fluorescence lifetime are insensitive to these interferences, making the measurements reliable and stable.

The direct determination of luminescence decay kinetics or emission lifetime requires complex and costly instrumentation. However, comparatively simple and compact phase-resolved luminescence measurement equipment that can determine the emission lifetime indirectly can be manufactured at low cost.

Various embodiments utilize phase-resolved luminescence detection which measures the time delay between the excitation of the sensor material with blue light and the emission of red light. None of the instrumental parameters that affect the intensity change the time delay between these two signals. Thus, the measurement (phase shift) does not depend on the excitation source intensity or the detector response, and it is insensitive to movements of the optical fiber due to manipulation of the biopsy needle. Furthermore, the phase shift does not depend of the amount of sensor material attached at the tip of the fiber. This is relevant to sensor repeatability as it significantly reduces the cost of calibration.

The disclosed system utilizes a compact fiber optic phase-resolved luminescence readout device that has characteristics for use in the proposed sensor system. The disclosed system also utilizes optical sensors which are based on indicator chemistry whose emission—and the variations therein caused by the interaction with the target analyte—can be determined by phase-resolved luminescence measurement.

Figure 6A:
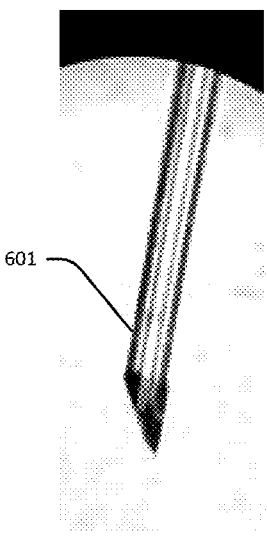
FIG. 6A-6C show a sensor tip before and after coating.
Figure 6B:
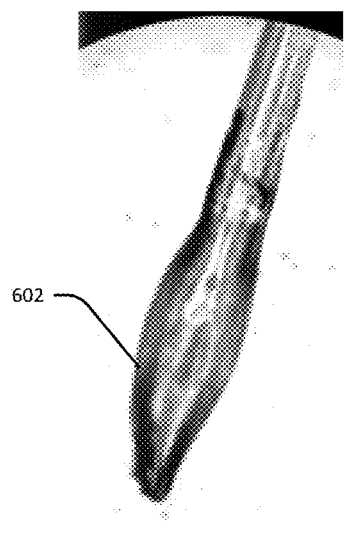
Figure 6C:
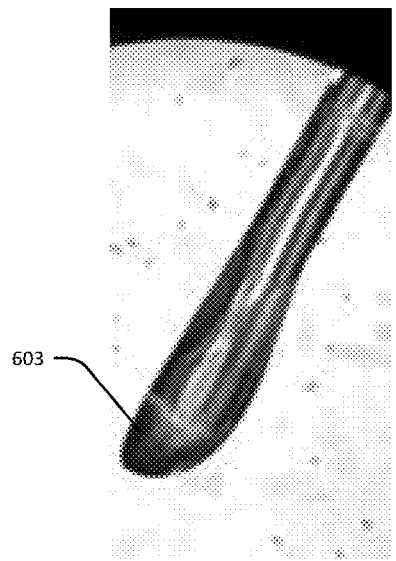

For use in various embodiments of the disclosed system, three luminescent sensor materials were chosen, each of them specifically sensitive to one of the three target metabolic markers selected. These sensor materials may be fabricated as individual microprobes with 250 µm plastic optical fibers. Plastic fibers have lower transmission than glass fibers, but tremendously simplify sensor fabrication and integration, since they are not subject to breaks, being flexible and robust. FIGS. 6A-6C shows exemplar fabricated fiber optic sensors, before integration into the biopsy needle. Luminescent sensor materials are attached to the tip of the plastic optical fibers, by curing the polymeric matrix directly of the fiber, in a simple process. Fabrication protocols were optimized to assure proper sensor attachment. FIG. 6A shows the sensor tip 601 prior to addition of the sensor material. FIGS. 6B and 6C show the tip following addition of the sensor material 602 and 603.

The exemplar individual fiber optic sensors were assessed for measurement range and accuracy, using saline solutions prepared with known levels of dissolved oxygen, pH, or lactate concentration, demonstrating measurement range and sensitivity at relevant levels.

A challenge which was overcome in fabricating the exemplar biopsy needles was to do so with the thin needles needed for the animal model tests on mice. Two designs were selected for fabricating exemplar SIB needles: (1) sensor integrated needle and (2) sensor integrated trocar. The sensor integrated trocar approach has significant advantages, probably the most relevant being that only the trocar used with a coaxial introducer needle in standard biopsies is the part modified, which makes the integrated sensor needle compatible with all current coaxial introducer needles and completely compatible with current protocols and imaging systems.

Figure 7A:
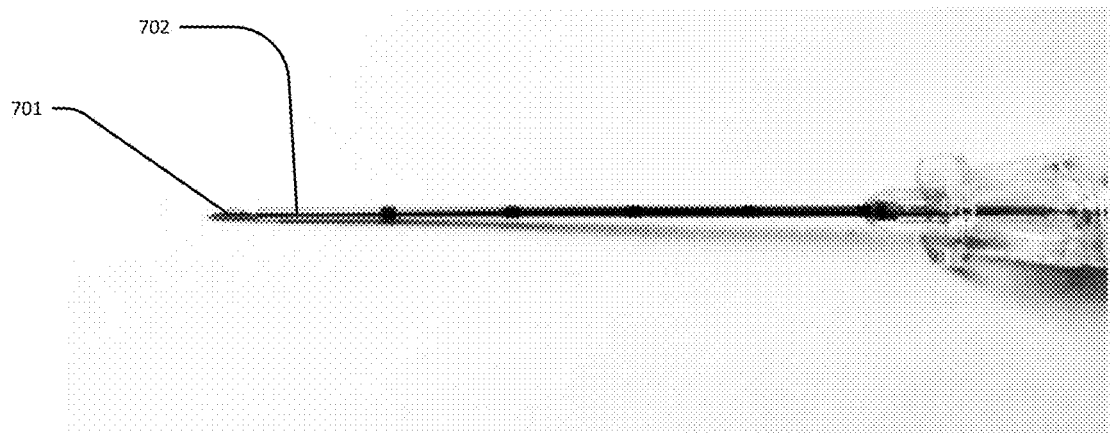
FIGS. 7A-B shows an exemplar trocar, needle and set of sensor tips inside the trocar.
Figure 7B:
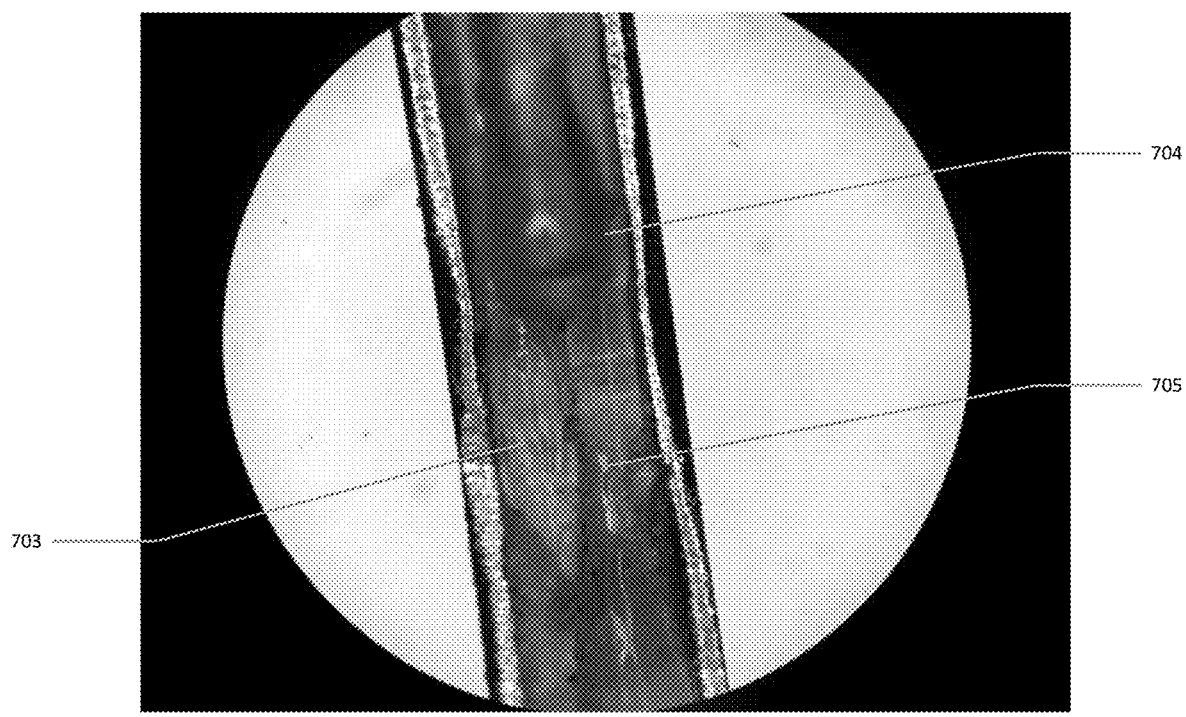

FIGS. 7A and 7B shows an exemplar sensor integrated trocar, with three 250 µm diameter plastic optical fiber sensors embedded. The dimensions of the tube opening, the tip of the trocar, and the distance from the opening to the trocar tip were optimized after bench testing.

FIG. 7A shows a sensor integrated trocar prototype 701 fabricated with a tube that fits inside a 20 gauge BART TrueGuide™ coaxial needle 702. FIG. 7B shows a detail of a longitudinally cut trocar showing three (transparent) optical fibers and three sensor tips 703 704 705.

In various embodiments, the sensor area is covered with a medical grade polymer. As has been shown in tested exemplar embodiments, the three sensors retain their analytical characteristics after integration with the biopsy needle prototypes. Sensor durability of exemplar embodiments was tested rigorously in the laboratory. The integrated sensor needle exemplar prototypes, once tested for chemical response, were inserted multiple times to a depth of 3-4 cm in beef liver and in chicken breast at an insertion speed of ~0.5 cm/sec. Probes were inspected carefully under an optical microscope for any signs of physical damage, and particularly for partial or complete delamination of the sensor coatings covering the optical fibers. No sign of sensor damage was observed. After the insertions, probes were tested again for chemical response. The sensors maintained complete functionality, demonstrating the robustness of the probes.

In furtherance of demonstrating the effectiveness of the disclosed system, animal models were used in testing. The protocol for the animal model studies includes the use of 30 FVB/N-Tg(MMTV-PyVT)634 Mul/J female mice between 6 and 10 weeks of age. This mouse strain was selected because it is a spontaneous breast cancer model. Performance of the exemplar testing utilized the Bard Mission Disposable Core Biopsy Instrument and the Bard Max-Core Disposable Core Biopsy Instrument, both compatible with the Bard TruGuide Disposable Coaxial Biopsy Needle. The sensor integrated trocar prototypes were inserted in TruGuide needles from the same supplier. Thus testing demonstrated the use of off-the-shelf components in combination with various disclosed elements. Throughout the testing procedure, the real-time sensor signals from the three fiber optic sensors were recorded in real time. The three regions under study were easily identified visually by the participating physicians and veterinarians, and are identified as follows:

Region 1: ~5 mm before entering the tumor.

Region 2: at the margin of the tumor, before the needle enters the tumor itself

Region 3: when the needle is within the tumor.

Figure 8A:
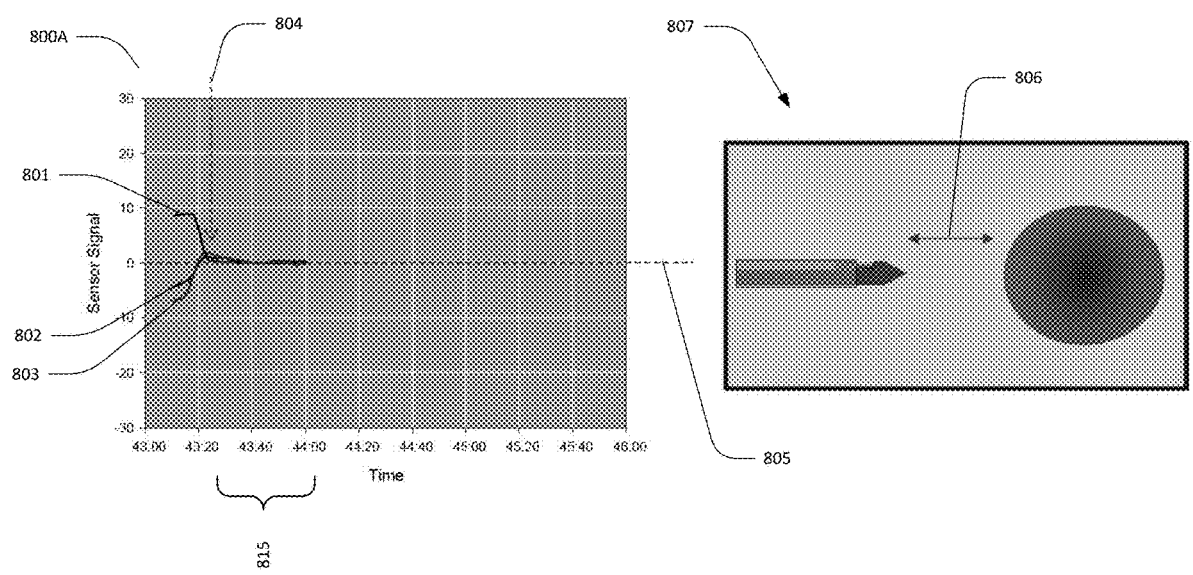
FIGS. 8A-8C shows the real-time sensor output during three pre-defined regions during needle insertion into a tumor.
Figure 8B:
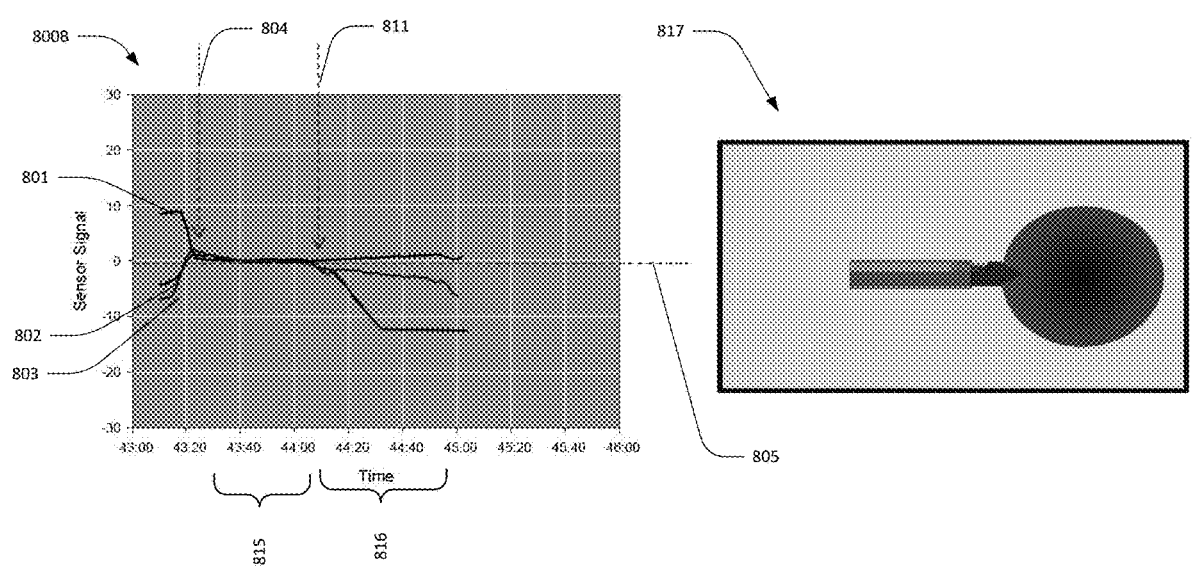
Figure 8C:
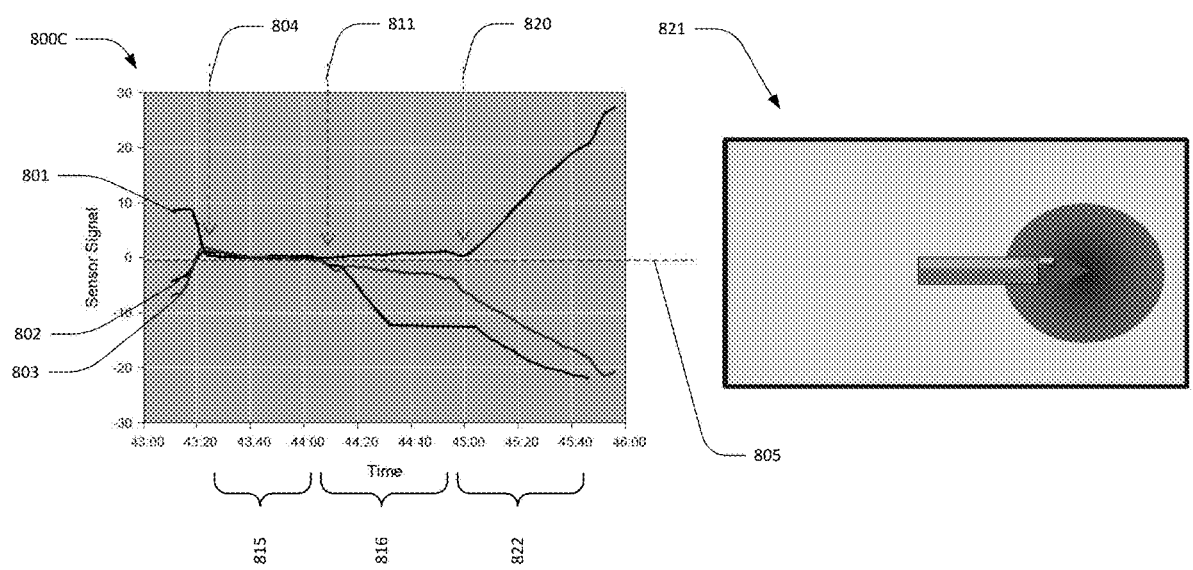

Normalized phase-sift measurements profile for an exemplar procedure of an embodiment of the disclosed system is illustrated in FIGS. 8A-8C. All three sensors (lactate, oxygen and pH) are based on phase-resolved luminescence detection, and the sensor signal is phase shift in degrees, normalized at the time of entrance in the animal body. In this exemplar embodiment during various stages of insertion (8A-8C) the lactate sensor signal 801, oxygen sensor signal 802, and pH sensor signal 803 are shown. Phase shifting provides the ability to analyze the signals from the three sensors in the same units. The sensor signal from each of the three sensors at the time of insertion into the mouse is considered the baseline signal 805 (zero). Signal (phase) variation is then calculated with respect to that first value. The sensor signal in Region 1 801 807 is considered our control value, assuming that no tumor tissue is found in that location. FIG. 8A shows step 1 800A. The coaxial needle incorporating the sensor integrated trocar is inserted in the mouse, baseline data 805 is established, and data is recorded from Region1 815 807, 5 mm away from the tumor. FIG. 8B shows step 2 800B. The coaxial needle is approaching and eventually touching the edge of the tumor and data is being recorded from Region 2 816 817. Some signal deviation 816 from baseline 805 may be observed. FIG. 8C shows step 3 800C. The coaxial needle is inserted into the sensor, and data is recorded from Region 3 821 822. Significant variation from baseline 805 values is observed for all three sensors 822. The coaxial needle is secured, the trocar is then removed, and data recording stops. The biopsy stylet and cutting cannula are inserted and a sample is collected.

In order to validate the efficacy of an exemplar embodiment, a total of 23 tests inserting the sensor integrated device into the tumor were conducted. Infiltrating Ductal Carcinoma was identified in all samples from full tumors at the area of insertion of the sensor integrated device. In all cases, sensor insertion into the tumor corresponded to a significant deviation of the signal from the control values for all three sensors. In none of the test did any of the three sensors exhibit significant deviation from the control signal in the control area. Furthermore, the multisensory probe was able to discriminate with 100% accuracy between the edge of the tumor and total insertion inside the cancer tissue. Thus, in this study the multisensory probes were able to report the location of the needle with 100% accuracy—0% false positives and 0% false negatives. We performed an analysis based on the percentage of variation of the sensor signal, which enabled us to combine and compare the information from the sensor reporting units for lactate (mg/L), oxygen (mmHg), and pH.

Figure 9A:
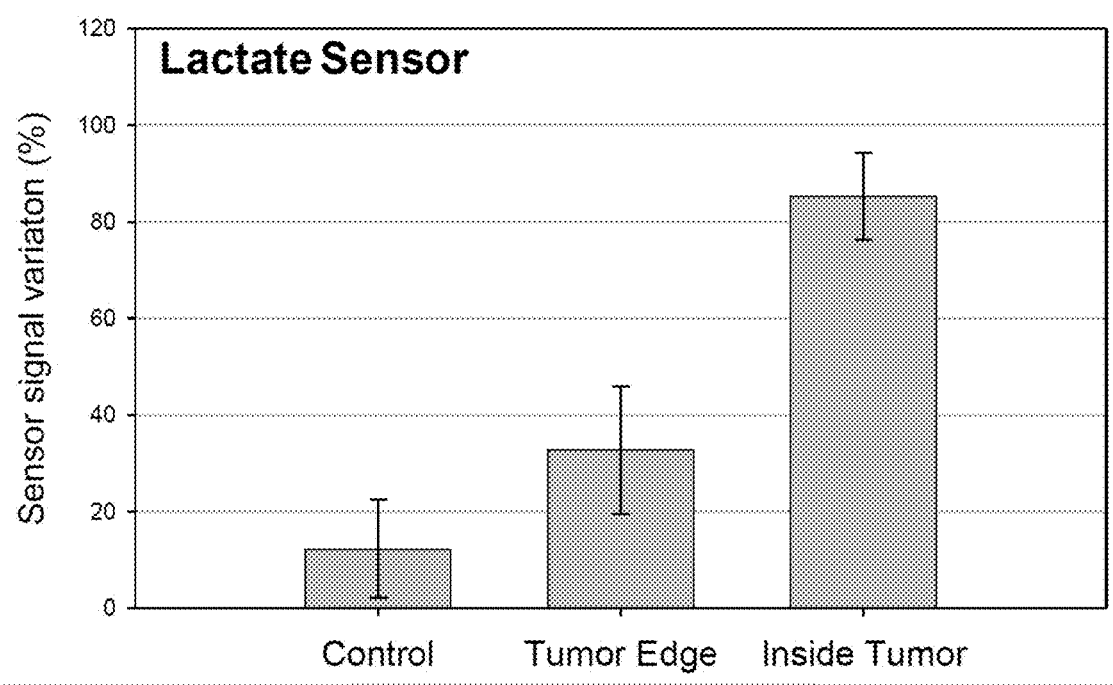
FIGS. 9A-C shows average sensor signal variation at the three pre-defined regions for the different sensor types.
Figure 9B:
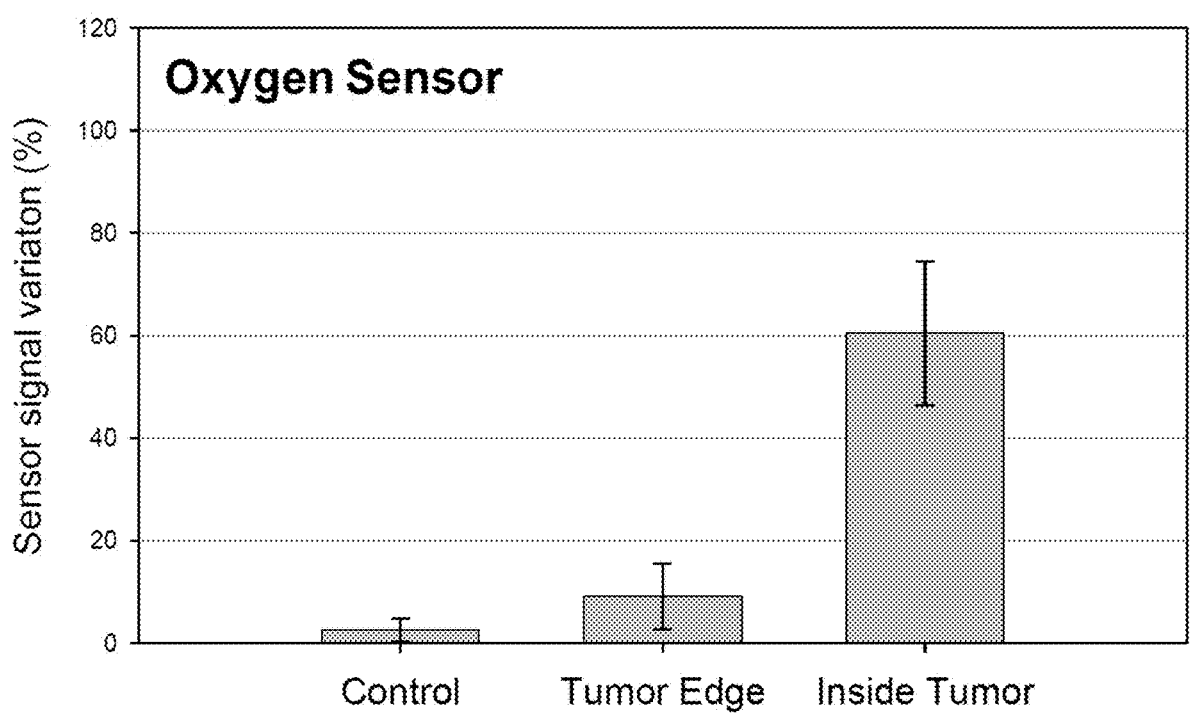
Figure 9C:
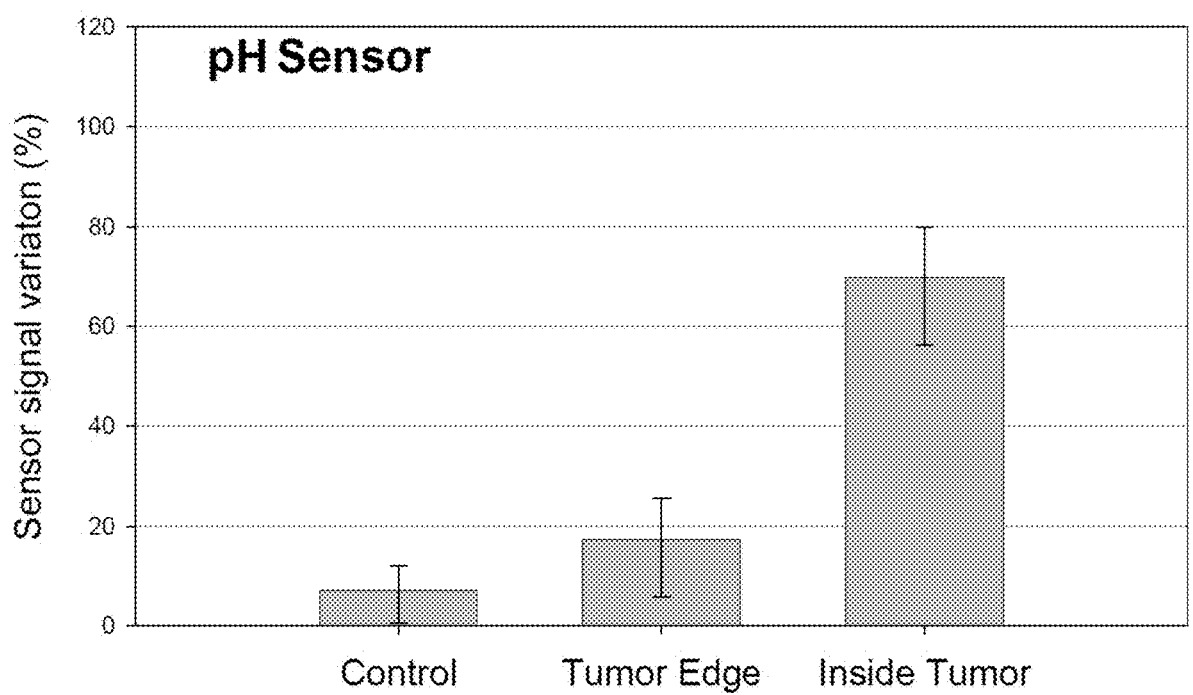

FIGS. 9A-C shows the mean and deviation for the 23 tumors evaluated for the control area (5 mm from the tumor), the edge of the tumor, and the tumor mass. Statistically significant differences are clearly among the three regions, demonstrating the capability to locate the needle and identify carcinoma tissue. The most important result is the robustness of the technique differentiating between areas with some cancer cells present (edge of tumor) and areas with high concentrations of cancer cells (inside the tumor), which will enable the surgeon to place the needle in regions of maximum tumor cellularity within the biopsied region. Shown is the sensor data analysis for 23 tests. The information from each of the sensors has been normalized as a percentage of signal variation for comparison. Mean and deviation are shown for the three sensors at the three selected regions: control region, edge of the tumor, and inside the tumor.

Figure 10:
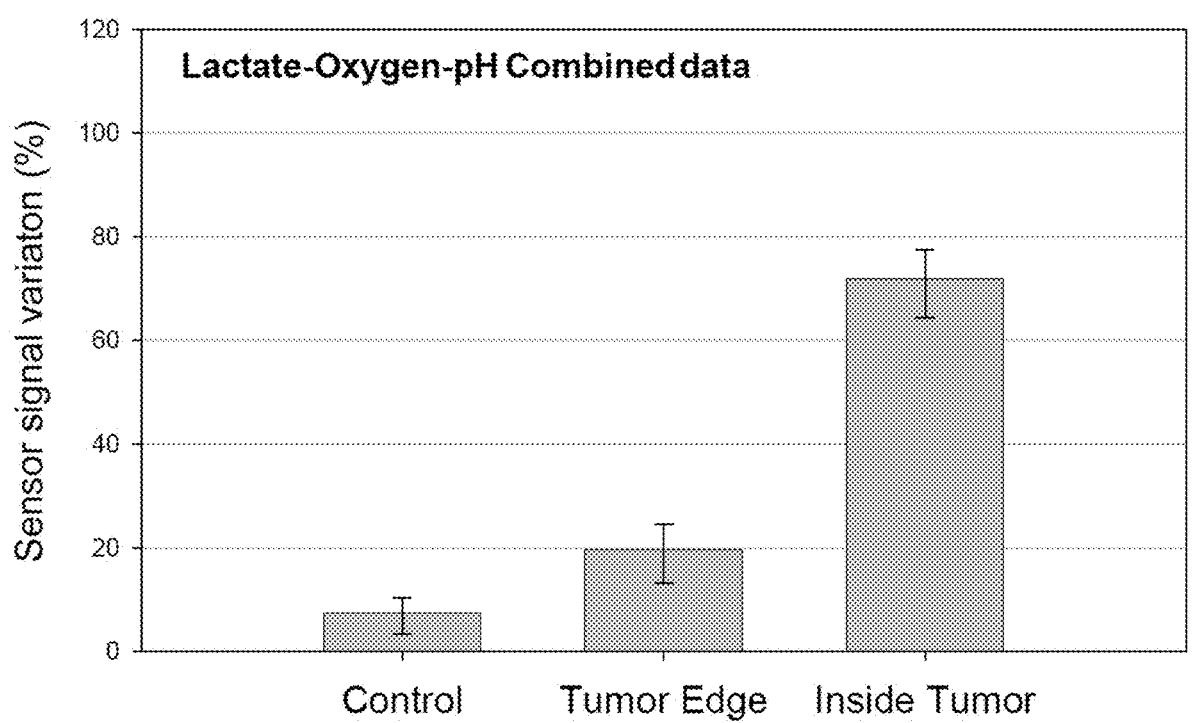
FIG. 10 shows sensor signal variation for the combined data from the different sensor types.
Figure 11A:
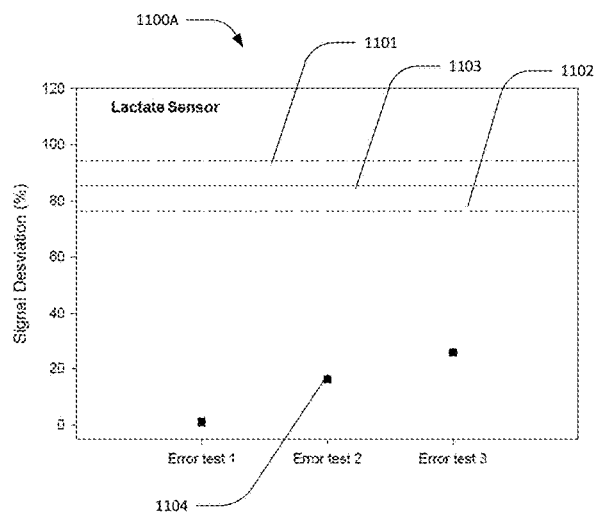
FIGS. 11A-D shows sensor signal deviation and error for the different sensor types when inserted inside the tumor, and the signal deviation when the needle is manipulated close to the tumor (less than one millimeter apart from the tumor) or touching the tumor, but it is not finally inserted inside the tumor.
Figure 11B:
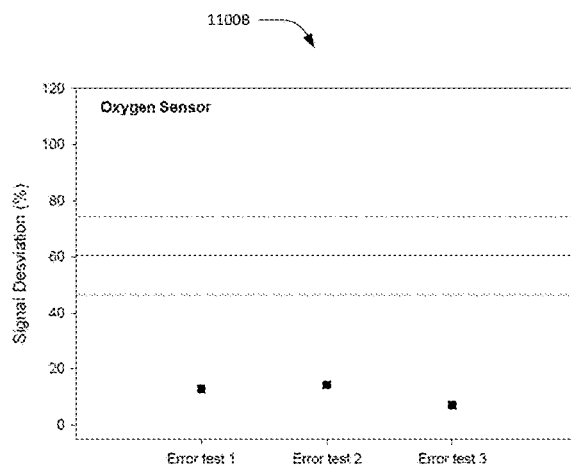
Figure 11C:
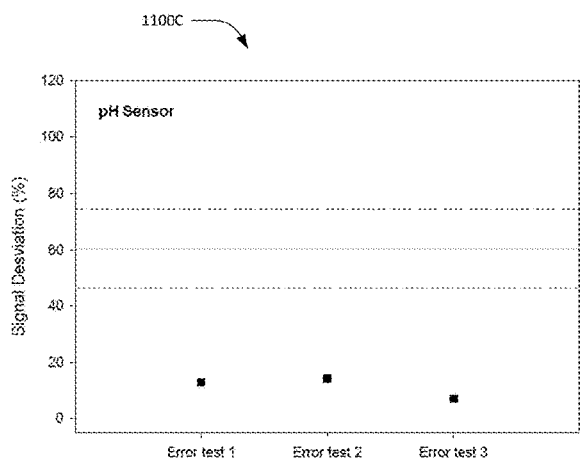
Figure 11D:
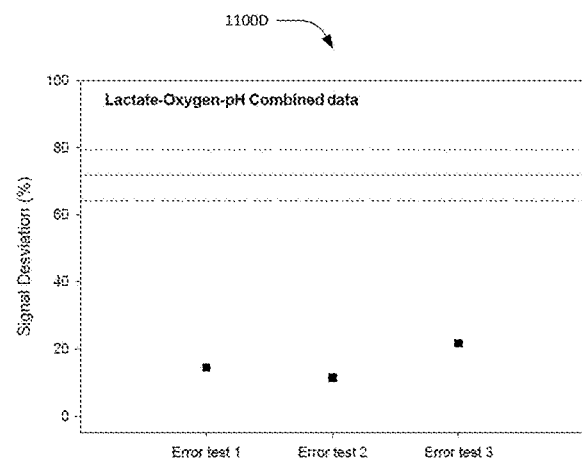

FIG. 10 shows the data analysis combining the signals from the three sensors (mean and deviation) in the control region, at the edge of the tumor, and inside the tumor. The deviation observed in FIG. 10 is less than that observed in FIG. 9A-C for the individual sensors. Thus, in alternate embodiments a logic-based model based on data integration from multiple sensors is utilized to optimize reliability. The information from each of the sensors has been normalized as a percentage of signal variation, and then combined for each test at each location into a single average value. Mean and deviation are shown for the control region, the edge of the tumor, and inside the tumor.

In order to further validate the disclosed methodology and system, three situations were simulated which could lead to false negative histopathology analysis: (A) in one test the needle was directed at the last step to be 1 mm away from the tumor mass, (B) in one additional test the needle was located at the last step to be touching the tumor at the bottom of the tumor mass but not inside it, and (C) in another test the needle was located at the last step to be touching the tumor at the top of the tumor mass but not inside it.

The sensor data collected for the exemplar embodiment being validated at the supposed tumor region for the three imprecise procedures indicates clearly that the needle was outside the target, which would have immediately triggered a warning for the surgeon. FIG. 11 shows that the data collected for the three sensors in the simulated erroneous procedures clearly fall outside the tumor tissue category.

In FIGS. 11A-D the solid lines 1103 and dashed lines 1101 1102 mark the mean sensor signal deviation and the 99% confidence interval for the three individual sensors 1100A 1100B 1100C and the combination of all three 1100D, when the needle is placed inside the tumor. The dots 1104 are signal deviations for the three sensors and the combination of all three for the three simulated erroneous biopsy procedures.

Figure 12:
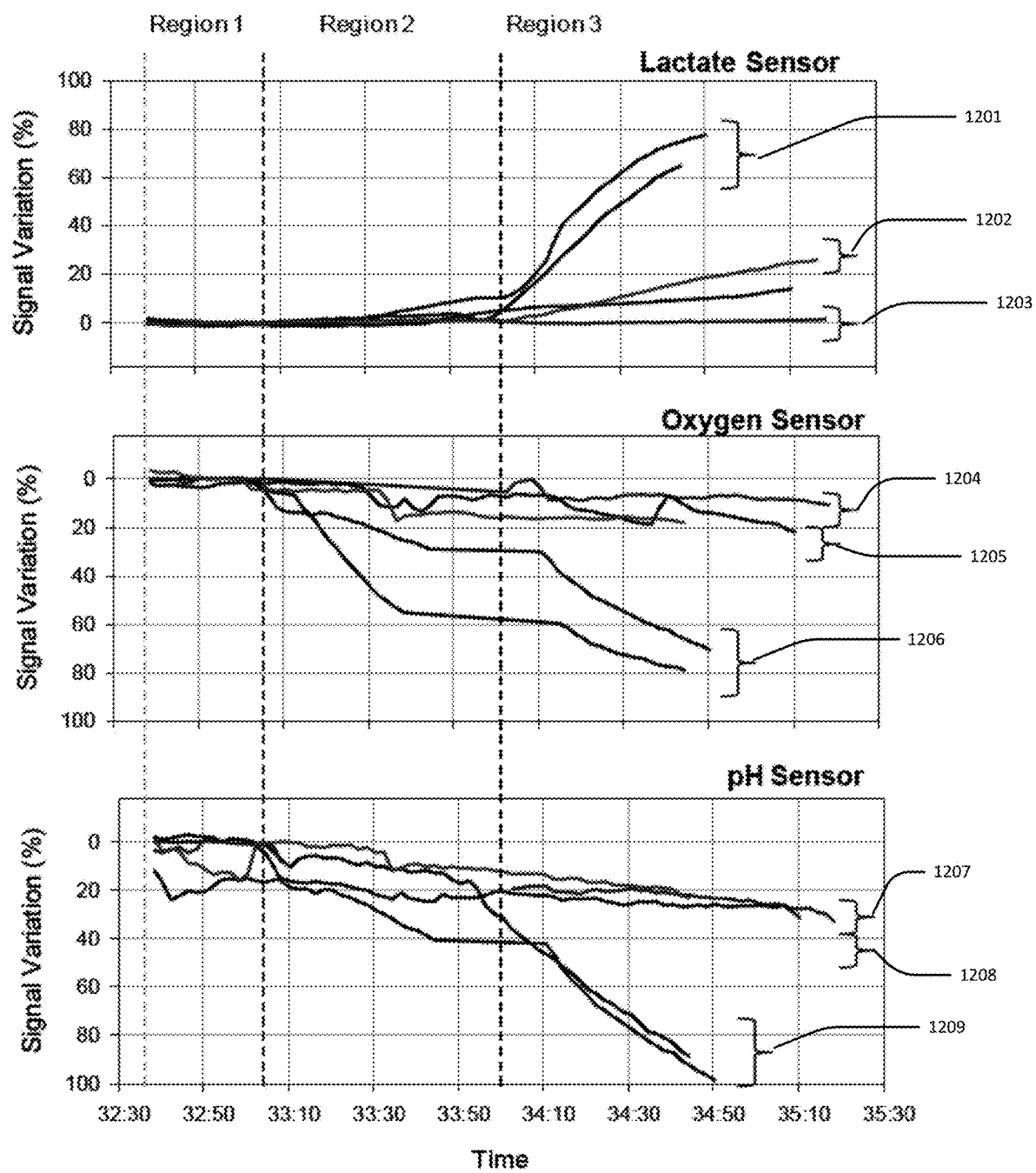
FIG. 12 shows sensor signal for the different sensor types during the various insertion regions.

FIG. 12 shows the data profile for those three tests in comparison with the data from two typical tests, in which the needle was inserted inside the tumor. These data profiles even more clearly differentiate between biopsy procedures ending inside the tumor and the three simulated erroneous biopsies. Shown are sensor signal deviation from baseline for three simulated erroneous biopsy procedures and two typical tests with final needle placement inside the tumor. The final placement for the needle sensor placement is shown by the various sensor data readings: 1201 inside the tumor; 1202 above/below the tumor; 1203 1 mm underneath the tumor; 1204 1 mm underneath the tumor; 1205 above/below the tumor; 1206 inside the tumor; 1207 1 mm underneath the tumor; 1208 above/below the tumor; 1209 inside the tumor.

In a standard biopsy procedure, doctors typically take several tissue samples with the same needle device. Exemplar embodiment needles were tested at least three times. In order to test needle durability, one of the fabricated exemplar needles was tested by performing eight consecutive biopsy procedures; the tested needle maintained functionality throughout the eight tests. Robustness and the capability of reusing the sensor device for one mouse were demonstrated.

What has been described herein is considered merely illustrative of the principles of this invention. Accordingly, it is well within the purview of one skilled in the art to provide other and different embodiments within the spirit and scope of the invention.

What is claimed is:

1. A sensor integrated biopsy (SIB) needle comprising:
   a coaxial needle;
   a hollow trocar, wherein the hollow trocar includes at least one sensor window having a permeable medical-grade material covering;
   at least one sensor, wherein each of the at least one sensors comprises:
   at least one source optical fiber connected to a light source and at least one detector optical fiber connected to a light detector, wherein the at least one source optical fiber and the at least one detector optical fiber are bundled in a single optical fiber lead, wherein the single optical fiber lead is tipped with at least one chemically sensitive luminescent dye-doped polymer material, wherein the at least one sensor is capable of sensing at least one target analyte in real time by a detected luminescent change of the at least one chemically sensitive luminescent material in contact with the at least one target analyte in a tissue; and
   wherein the at least one sensor detects levels of the at least one chemically sensitive luminescent dye-doped material luminescence changes in the presence of lactate, and wherein a concentration of lactate is measured by phase-resolved luminescence detection measuring time delay between excitation of the chemically sensitive luminescent dye-doped polymer material by blue light and emission of red light.

2. The SIB needle as in claim 1 wherein the hollow trocar may be removed during a procedure and replaced with a tissue removal device.

3. The SIB needle as in claim 1 wherein the at least one sensor comprises:
a first optical fiber lead tipped with at least one chemically sensitive luminescent dye-doped material which changes luminescence quantifiably measurable in correlation to concentrations of lactate in contact with the optical fiber tip, measured by phase resolved luminescence detection, and
a second optical fiber lead tipped with at least one chemically sensitive luminescent dye-doped material which changes luminescence quantifiably measurable in correlation to a pH of tissue in contact with the optical fiber tip, measured by phase resolved luminescence detection measuring time delay between excitation of the chemically sensitive luminescent dye-doped polymer material by blue light and emission of red light, and
a third optical fiber lead tipped with at least one chemically sensitive luminescent dye-doped material which changes luminescence quantifiably measurable in correlation to concentrations of oxygen in contact with the optical fiber tip, measured by phase resolved luminescence detection measuring time delay between excitation of the chemically sensitive luminescent dye-doped polymer material by blue light and emission of red light,
whereby simultaneous measurement of phase resolved luminescence detected from the at least the first optical fiber, the second optical fiber and the third optical fiber are correlated in real-time to measure tissue glycolysis.

4. The SIB needle as in claim 1 wherein the at least one sensor comprises:
a first optical fiber lead tipped with at least one chemically sensitive luminescent dye-doped material which changes luminescence quantifiably measurable in correlation to concentrations of lactate in contact with the optical fiber tip, measured by phase resolved luminescence detection measuring time delay between excitation of the chemically sensitive luminescent dye-doped polymer material by blue light and emission of red light,
a second optical fiber lead tipped with at least one chemically sensitive luminescent dye-doped material which changes luminescence quantifiably measurable in correlation to concentrations of lactate in contact with the optical fiber tip, measured by phase resolved luminescence detection measuring time delay between excitation of the chemically sensitive luminescent dye-doped polymer material by blue light and emission of red light,
a second optical fiber lead tipped with at least one chemically sensitive luminescent dye-doped material which changes luminescence quantifiably measurable in correlation to concentrations of lactate in contact with the optical fiber tip, measured by phase resolved luminescence detection measuring time delay between excitation of the chemically sensitive luminescent dye-doped polymer material by blue light and emission of red light,
whereby simultaneous measurement of phase resolved luminescence detected from the at least the first optical fiber, the second optical fiber and the third optical fiber are correlated in real-time to monitor tissue metabolism.

5. A method for obtaining a biopsy sample comprising:
inserting a sensor integrated biopsy (SIB) needle into a region tissue to be tested for a cancerous tumor, wherein the sensor integrated biopsy needle comprises at least a coaxial needle, a hollow trocar, wherein the hollow trocar comprises at least one sensor window having a permeable medical-grade material covering, and
at least one sensor, wherein each of the at least one sensors comprises:
at least one source optical fiber connected to a light source and at least one detector optical fiber connected to a light detector,
wherein the at least one source optical fiber and the at least one detector optical fiber are bundled in a single optical fiber lead, wherein the single optical fiber lead is tipped with at least one chemically sensitive luminescent dye-doped polymer material, and
wherein the at least one sensor is capable of sensing at least one target analyte in real time by a detected luminescent change of the at least one chemically sensitive luminescent material in contact with the at least one target analyte in a tissue, and wherein the at least one sensor detects levels of the at least one chemically sensitive luminescent dye-doped material luminescence changes in the presence of lactate, and wherein a concentration of lactate is measured by phase resolved luminescence detection measuring time delay between excitation of the chemically sensitive luminescent dye-doped polymer material by blue light and emission of red light;
monitoring on a display, at least one sensor signal from the at least one sensor for sensor signal levels indicating a tip of the SIB needle is located inside a cancerous tumor;
removing the hollow trocar from the coaxial needle;
inserting a biopsy tissue removal component into the coaxial needle;
removing a portion of tissue for testing using the biopsy tissue removal component.

6. The method as in claim 5 also comprising: monitoring on the display, a simultaneous display of the at least one sensor signal and a tissue imaging device output of a tissue region in proximity to the SIB needle.

7. The method as in claim 5 wherein the at least one sensor comprises:
a first optical fiber lead tipped with at least one chemically sensitive luminescent dye-doped material which changes luminescence quantifiably measurable in correlation to concentrations of lactate in contact with the optical fiber tip, measured by phase resolved luminescence detection measuring time delay between excitation of the chemically sensitive luminescent dye-doped polymer material by blue light and emission of red light, and a second optical fiber lead tipped with at least one chemically sensitive luminescent dye-doped material which changes luminescence quantifiably measurable in correlation to a pH of tissue in contact with the optical fiber tip, measured by phase resolved luminescence detection measuring time delay between excitation of the chemically sensitive luminescent dye-doped polymer material by blue light and emission of red light, and a third optical fiber lead tipped with at least one chemically sensitive luminescent dye-doped material which changes luminescence quantifiably measurable in correlation to concentrations of oxygen in contact with the optical fiber tip, measured by phase resolved luminescence detection measuring time delay between excitation of the chemically sensitive luminescent dye-doped polymer material by blue light and emission of red light, whereby simultaneous measurement of phase resolved luminescence detected from the at least the first optical fiber, the second optical fiber and the third optical fiber are correlated in real-time to measure tissue glycolysis.

8. The method as in claim 5 wherein the at least one sensor comprises:

a first optical fiber lead tipped with at least one chemically sensitive luminescent dye-doped material which changes luminescence quantifiably measurable in correlation to concentrations of lactate in contact with the optical fiber tip, measured by phase resolved luminescence detection measuring time delay between excitation of the chemically sensitive luminescent dye-doped polymer material by blue light and emission of red light, a second optical fiber lead tipped with at least one chemically sensitive luminescent dye-doped material which changes luminescence quantifiably measurable in correlation to concentrations of lactate in contact with the optical fiber tip, measured by phase resolved luminescence detection measuring time delay between excitation of the chemically sensitive luminescent dye-doped polymer material by blue light and emission of red light, a second optical fiber lead tipped with at least one chemically sensitive luminescent dye-doped material which changes luminescence quantifiably measurable in correlation to concentrations of lactate in contact with the optical fiber tip, measured by phase resolved luminescence detection measuring time delay between excitation of the chemically sensitive luminescent dye-doped polymer material by blue light and emission of red light, whereby simultaneous measurement of phase resolved luminescence detected from the at least the first optical fiber, the second optical fiber and the third optical fiber are correlated in real-time to monitor tissue metabolism.

9. A system for obtaining a biopsy sample comprising:
a coaxial needle;
a hollow trocar, wherein the hollow trocar includes at least one sensor window, wherein the hollow trocar comprises at least one sensor window having a permeable medical-grade material covering;
at least one sensor comprising:
at least one source optical fiber connected to a light source and at least one detector optical fiber connected to a light detector, wherein the at least one source optical fiber and the at least one detector optical fiber are bundled in a single optical fiber lead, wherein the single optical fiber lead is at least one optical fiber tipped with at least one chemically sensitive luminescent dye-doped polymer material, and wherein the at least one sensor is capable of sensing at least one target analyte in real time by a detected luminescent change of the at least one chemically sensitive luminescent material in contact with the at least one target analyte in a tissue;

a light source, and wherein the at least one sensor detects levels of the at least one chemically sensitive luminescent dye-doped material luminescence changes in the presence of lactate, and wherein a concentration of lactate is measured by phase resolved luminescence detection measuring time delay between excitation of the chemically sensitive luminescent dye-doped polymer material by blue light and emission of red light;

a photodetector;

a display showing position of the needle in real-time and a readout of chemical measurements detected by the at least one sensor;

a tissue removal device which may replace the hollow trocar within the coaxial needle;

whereby the system may be used to determine the optimal location within tissue for removing a biopsy sample by a user monitoring the readout available on the display showing real-time chemical measurements and real-time needle position.

10. The system as in claim 9 wherein the at least one sensor comprises:

a first optical fiber lead tipped with at least one chemically sensitive luminescent dye-doped material which changes luminescence quantifiably measurable in correlation to concentrations of lactate in contact with the optical fiber tip, measured by phase resolved luminescence detection measuring time delay between excitation of the chemically sensitive luminescent dye-doped polymer material by blue light and emission of red light, and a second optical fiber lead tipped with at least one chemically sensitive luminescent dye-doped material which changes luminescence quantifiably measurable in correlation to a pH of tissue in contact with the optical fiber tip, measured by phase resolved luminescence detection measuring time delay between excitation of the chemically sensitive luminescent dye-doped polymer material by blue light and emission of red light, and a third optical fiber lead tipped with at least one chemically sensitive luminescent dye-doped material which changes luminescence quantifiably measurable in correlation to concentrations of oxygen in contact with the optical fiber tip, measured by phase resolved luminescence detection measuring time delay between excitation of the chemically sensitive luminescent dye-doped polymer material by blue light and emission of red light, whereby simultaneous measurement of phase resolved luminescence detected from the at least the first optical fiber, the second optical fiber and the third optical fiber are correlated in real-time to measure tissue glycolysis.

11. The system as in claim 9 wherein the at least one sensor comprises:

a first optical fiber lead tipped with at least one chemically sensitive luminescent dye-doped material which changes luminescence quantifiably measurable in correlation to concentrations of lactate in contact with the optical fiber tip, measured by phase resolved luminescence detection measuring time delay between excitation of the chemically sensitive luminescent dye-doped polymer material by blue light and emission of red light, a second optical fiber lead tipped with at least one chemically sensitive luminescent dye-doped material which changes luminescence quantifiably measurable in correlation to concentrations of lactate in contact with the optical fiber tip, measured by phase resolved luminescence detection measuring time delay between excitation of the chemically sensitive luminescent dye-doped polymer material by blue light and emission of red light, a second optical fiber lead tipped with at least one chemically sensitive luminescent dye-doped material which changes luminescence quantifiably measurable in correlation to concentrations of lactate in contact with the optical fiber tip, measured by phase resolved luminescence detection measuring time delay between excitation of the chemically sensitive luminescent dye-doped polymer material by blue light and emission of red light, whereby simultaneous measurement of phase resolved luminescence detected from the at least the first optical fiber, the second optical fiber and the third optical fiber are correlated in real-time to monitor tissue metabolism.

* * * * *